(12) United States Patent
Mäntylä

(10) Patent No.: US 9,574,994 B2
(45) Date of Patent: Feb. 21, 2017

(54) SHEET MEASUREMENT

(71) Applicant: METSO AUTOMATION OY, Vantaa (FI)

(72) Inventor: Markku Mäntylä, Kangasala (FI)

(73) Assignee: METSO AUTOMATION OY, Vantaa (FI)

( * ) Notice: Subject to any disclaimer, the term of this patent is extended or adjusted under 35 U.S.C. 154(b) by 0 days.

(21) Appl. No.: 14/402,989

(22) PCT Filed: May 22, 2013

(86) PCT No.: PCT/FI2013/050559
§ 371 (c)(1),
(2) Date: Nov. 21, 2014

(87) PCT Pub. No.: WO2013/175071
PCT Pub. Date: Nov. 28, 2013

(65) Prior Publication Data
US 2015/0136993 A1    May 21, 2015

(30) Foreign Application Priority Data
May 25, 2012   (FI) ..................................... 20125559

(51) Int. Cl.
*G01J 1/42*  (2006.01)
*G01N 21/33* (2006.01)
(Continued)

(52) U.S. Cl.
CPC .............. *G01N 21/33* (2013.01); *G01N 21/31* (2013.01); *G01N 21/8914* (2013.01);
(Continued)

(58) Field of Classification Search
CPC ................ G01J 1/429; G01J 1/58; G01J 1/02; G01J 1/04; G01N 21/33
See application file for complete search history.

(56) References Cited

U.S. PATENT DOCUMENTS 4,159,893 A * 7/1979 Ham ................... G01N 33/241
                                                                  436/131
4,707,603 A    11/1987 Miemeläet al.
(Continued)

FOREIGN PATENT DOCUMENTS

CN    1153302 A    7/1997
CN    1245288 A    2/2000
(Continued)

OTHER PUBLICATIONS

May 11, 2015 Search Report issued in European Application No. 13794044.1.
(Continued)

*Primary Examiner* — David Porta
*Assistant Examiner* — Mamadou Faye
(74) *Attorney, Agent, or Firm* — Oliff PLC (57) ABSTRACT

A detector receives optical radiation interacted with the measured sheet and is responsive to a predetermined optical absorption band of lignin, a predetermined optical absorption band of dry matter and two or more separate optical bands. The measuring unit measures a lignin dependent value on the basis of attenuation in the absorption band of lignin, and a dry matter dependent value on the basis of attenuation in the absorption band of the dry matter, and determines a general dependence of attenuation with respect to wavelength by measuring attenuations in the separate optical bands. The measuring unit forms a value representing a dry matter content on the basis of the lignin dependent value, the dry matter dependent value and the general dependence of attenuation.

21 Claims, 7 Drawing Sheets

(51) Int. Cl.
  *G01N 21/31* (2006.01)
  *G01N 21/89* (2006.01)
  *G01N 33/34* (2006.01)

(52) U.S. Cl.
  CPC ... *G01N 33/346* (2013.01); *G01N 2021/8917* (2013.01); *G01N 2201/061* (2013.01); *G01N 2201/068* (2013.01)

(56) References Cited

U.S. PATENT DOCUMENTS

| | | | |
|---|---|---|---|
| 4,805,623 A | | 2/1989 | Jöbsis |
| 5,276,327 A | | 1/1994 | Bossen et al. |
| 5,282,931 A | | 2/1994 | LeClerc et al. |
| 5,672,881 A | * | 9/1997 | Striepeke ............ G01N 21/6456 250/458.1 |
| 6,281,498 B1 | | 8/2001 | Fellows |
| 6,355,931 B1 | | 3/2002 | Hernandez et al. |
| 6,495,831 B1 | | 12/2002 | Hyvärinen et al. |
| 6,526,369 B1 | | 2/2003 | Meinecke et al. |
| 2001/0017195 A1 | | 8/2001 | Trung et al. |
| 2003/0047135 A1 | | 3/2003 | Kansakoski et al. |
| 2005/0155735 A1 | | 7/2005 | Ischdonat et al. |
| 2009/0152177 A1 | * | 6/2009 | Greenspan ............ B07C 5/342 209/580 |
| 2009/0185162 A1 | * | 7/2009 | Shakespeare et al. ........ 356/51 |
| 2011/0204232 A1 | * | 8/2011 | Mantyla .................. D21H 3/78 250/338.1 |
| 2014/0307309 A1 | * | 10/2014 | Downing et al. ............ 359/359 |

FOREIGN PATENT DOCUMENTS

| | | |
|---|---|---|
| CN | 102004084 A | 4/2011 |
| EP | 0 332 018 A2 | 9/1989 |
| EP | 0 751 382 A2 | 1/1997 |
| GB | 2 044 443 A | 10/1980 |
| GB | 2044443 A * | 10/1980 |
| WO | WO 2011/135179 A1 | 11/2011 |

OTHER PUBLICATIONS

Berben et al., "Determination of Lignin in Wood Pulp by Diffuse Reflectance Fourier Transform Infrared Spectrometry", IPC Technical Paper Series, Jan. 1987, No. 210, pp. 1-13.

Jeffers et al., "Continuous, On-Line Measurement of Lignin in Wood Pulp", SPIE, Sep. 4, 1991, vol. 1587, pp. 215-218.

International Search Report issued in International Patent Application No. PCT/FI2013/050559 dated Sep. 6, 2013.

International Preliminary Report on Patentability issued in International Patent Application No. PCT/FI2013/050559 dated Aug. 26, 2014.

Finnish Office Action issued in Finnish Application No. 20125559 dated Oct. 23, 2014.

Finnish Office Action issued in Finnish Application No. 20125559 dated Mar. 14, 2014.

Finnish Office Action issued in Finnish Application No. 20125559 dated Jan. 28, 2013.

* cited by examiner

SHEET MEASUREMENT

FIELD

The invention relates to a sheet measurement.

BACKGROUND

Cellulose is one of the dry matters in paper and its percentage in the paper may be measured by directing infrared light from an optical source to the paper. Interaction between the paper and the infrared light causes the attenuation of the infrared light to depend on both wavelength and the percentage of cellulose. Cellulose attenuates strongly at known, narrow absorption bands in infrared region. When an attenuation of an absorption band of cellulose is measured, it is possible to determine cellulose content of the measured paper.

When paper comprises a plurality of dry matters and lignin the amount of which is usually unknown the measurement faces serious problems and fails to provide reliable results. Hence, there is a need for a better measurement.

SUMMARY

The following presents a simplified summary of the invention in order to provide a basic understanding of some aspects of the invention. Its purpose is to present some concepts of the invention in a simplified form as a prelude to the more detailed description that is presented later.

An aspect of the invention relates to apparatii, systems, and methods.

Although the various aspects, embodiments and features of the invention are recited independently, it should be appreciated that all combinations of the various aspects, embodiments and features of the invention are possible and within the scope of the present invention as claimed.

The present solution provides advantages. An optical lignin measurement becomes possible and accurate. A good estimate of dry matter content may also be obtained by taking into account the lignin content.

BRIEF DESCRIPTION OF THE DRAWINGS

In the following the invention will be described in greater detail by means of exemplary embodiments with reference to the attached drawings, in which.

DESCRIPTION OF EMBODIMENTS

Exemplary embodiments of the present invention will now be described more fully hereinafter with reference to the accompanying drawings, in which some, but not necessarily all embodiments of the invention are shown. Indeed, the invention may be embodied in many different forms and should not be construed as limited to the embodiments set forth herein. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments.

Figure 1A:
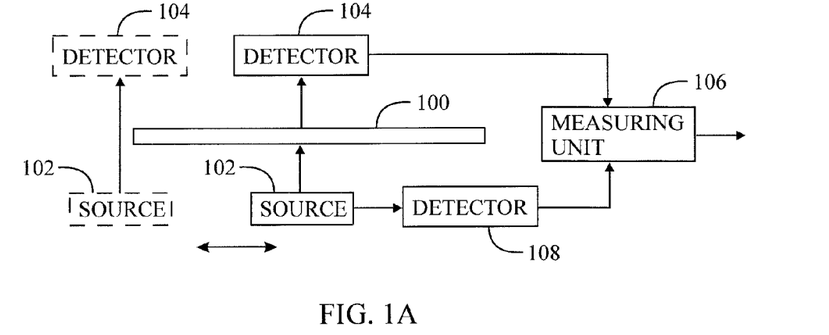
FIG. 1A shows a measurement configuration using optical radiation propagated through the object.

FIG. 1A presents a basic configuration of a measurement. A measured sheet 100 comprising cellulose material and potentially lignin is placed between an optical source 102 outputting optical radiation and a detector 104 receiving optical radiation which has interacted with the sheet 100. The measured sheet 100 may be a sheet of paper, for example. In an embodiment, the paper may be tissue paper. The cellulose material of the measured sheet 100 may be in wood fibers which may be the raw material of the measured sheet 100. The sheet may also contain lignin originating from the wood fibers. A lignin content of a sheet 100 may vary from zero to tens of percents. The detector 104 and the measuring unit 106 may be parts of a measuring device which may also comprise the optical source 102.

The optical source 102 may output a broad and continuous band of radiation. The output optical band may comprise the infrared region including wavelengths between about 750 nm and 500 µm. In an embodiment the optical band of the optical source 102 comprises a near infrared, a short-wavelength infrared and mid-wavelength infrared regions including wavelengths between about 750 nm to 10 µm, for example. Additionally or alternatively, the optical output band from the optical source 102 may comprise ultraviolet light. The ultraviolet light may comprise a band from about 200 nm to 400 nm, for example.

Instead of continuous band, the optical source 102 may output at least two discrete optical bands in the measured optical bands. The optical source 102 may comprise one or more incandescent lamps, light-emitting diodes (LED), lasers, gas discharge lamps or the like, for example. The optical source 102 may additionally comprise at least one optical component for changing the shape of the beam of the light by convergence, divergence or collimation and directing the beam of light to the measured sheet 100. The at least one optical component may comprise a lens, a mirror, a beam splitter/combiner, an optical filter, optical fiber or the like.

The detector 104 receives optical radiation interacted with the measured sheet 100 comprising cellulose material. The interaction may comprise reflection of optical radiation from the sheet 100 or transmission of the optical radiation through the sheet 100. The interaction is based on linear optics which may also be called ordinary optics i.e. the frequency of optical radiation does not change during or after the interaction. A part of such ordinary optics is absorption spectroscopy into which the presented solution belongs to. The detector 104 outputs electrical signals in response to detected powers of the measured optical bands such that the detector 104 is responsive to one or more predetermined optical absorption bands of lignin and two or more predetermined separate optical bands apart from the predetermined absorption bands of lignin. An absorption band of lignin refers to an optical band where the attenuation has a local or absolute maximum because of lignin. In general, an absorption band of a substance refers to an optical band where the attenuation has a local or absolute maximum because of the substance.

If the output powers or power distributions of the optical source 102 in the measured optical bands are known, the electrical signals output by the detector 104 relate to attenuations in the measured optical bands.

The output power as a function of wavelength may be measured by taking a sample from the output optical radiation by the detector 104 when the measured object 100 is not between the optical source 102 and the detector 104. The measurement may be performed such that the detector 104 and the optical source 102 move over the edge of the measured object 100 (shown in dashed lines). In a traversing measurement of the sheet 100 that may be performed after each traverse or from time to time. The measurement without the measured object 100 defines a reference optical power $I_0$ at each measured band $\Delta\lambda i$ directed to the measured object 100.

In an embodiment, a detector 108 similar to the detector 104 may be used to take a sample of the output optical radiation of the optical source 102 for an alternative or additional reference optical power $I_0$. The sample of the output optical radiation may in this embodiment mean some known percentages of the output optical power from the source 102, for example, while the rest of the output radiation proceeds to the sheet 100.

Additionally or alternatively, the power or the power distribution may be known beforehand since certain types of optical sources (such as lasers) may output a known optical power or a known optical power distribution in a known optical band. Hence, the sampling of the output optical power of the optical source 102 is not presented in more detail.

The detector 104 may comprise one or more detecting elements. The detector 104 may be based on a semiconductor technology. The detector 104 may comprise at least one photo diode such as a PIN diode, an avalanche diode or the like. The detecting elements of the detector 104 may be arranged in an array or in a matrix. The detector 104 having a plurality of detecting elements may be comprise discrete elements or they may be integrated together using IC-technology (Integrated Circuit). The matrix of elements of the detector 104 may be based on a InGaAs (Indium Gallium Arsenide), extended InGaAs, HgCdTe (Mercury Cadmium Telluride), PbS (Lead Sulfide), PbSe (Lead Selenide) technique in the infrared region, for example. In the visible and ultraviolet region suitable photodiodes and photocathodes may be used, for example.

The detector 104 may additionally comprise at least one optical component for changing the shape of the beam of the light and/or directing the beam of light to the at least on detecting element. The at least one optical component may be a lens, a mirror, a beam splitter/combiner, an optical filter, optical fiber or the like.

On the basis of responses from the detector 104, the measuring unit 106 measures attenuation of the detected bands of the optical radiation. The detector 104 and the measuring unit 106 together form an optical power meter which measures optical power as a function of wavelength. Attenuation is a reciprocal value with respect to transmittance of the sheet 100. However, they both imply the same property of the sheet 100 and may be referred to as attenuation. The measuring unit 106 may comprise at least one processor, at least one memory and at least one computer program for processing the measured data. In an embodiment, the measuring device comprises the detector 104 and at least one suitable computer program, since the at least one computer program may be loaded in an otherwise existing system associated with a paper machine for processing the data fed from the detector 104.

Figure 1B:
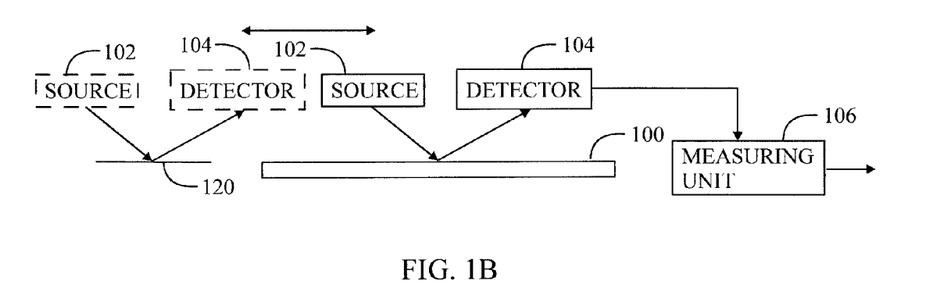
FIG. 1B shows a measurement configuration using reflected optical radiation.

In FIG. 1B a similar kind of measurement to FIG. 1A is presented except that the measurement is based on reflectance. The optical source 102 outputs optical power towards the measured object 100 which reflects the optical radiation towards the detector 104. A reference measurement may be performed such that the detector 104 and the optical source 102 move over the edge of the measured object (shown in dashed lines) and measures a reference surface 120 which has a predetermined reflectance. The measuring unit 106 performs the signal processing in a similar manner to the measurement of FIG. 1A.

Figure 2:
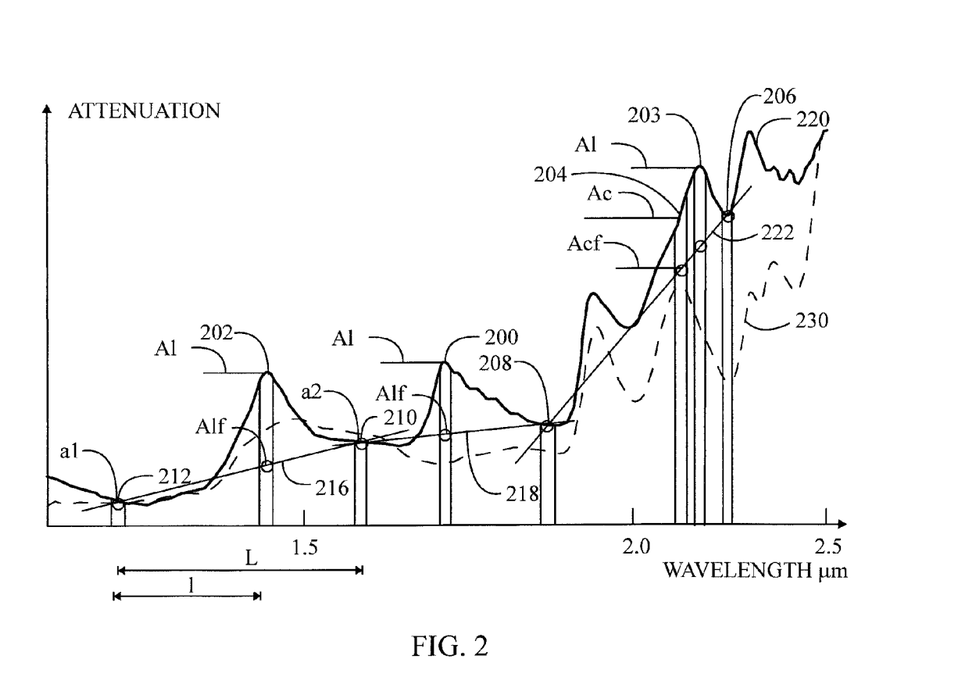
FIG. 2 shows attenuation as function of wavelength.

The following explains the operation of the measuring unit 106 with the help of FIG. 2. The continuous line 220 presents a measured attenuation of a sample containing lignin. The dashed line 230 presents a measured attenuation of paper without lignin. The y-axis is attenuation in an arbitrary scale, and the x-axis is wavelength in micrometers. The measuring unit 106 measures at least one lignin dependent value Al on the basis of attenuation of the optical radiation in the one or more predetermined optical absorption bands 200, 202, 203 of lignin. The lignin dependent value Al of each band 200, 202, 203 may be related to an optical power integrated over each of the optical band 200, 202, 203.

The measuring unit 106 also determines a general dependence of attenuation with respect to wavelength in the environment of the at least one lignin band 200, 202, 203 by measuring attenuations in two or more predetermined separate optical bands 208, 210, 212 apart from the predetermined optical absorption bands 200, 202, 203 associated with lignin. Correspondingly, also these measured values may be formed by integrating over the measured band. The integration may take place automatically in the detector element or it may be computed in the measuring unit 106.

In an embodiment, the measuring unit 106 may also measure at least one dry matter dependent value on the basis of attenuation of the optical radiation in the one or more predetermined optical absorption bands 204 of dry matter in addition to that/those of lignin. The measuring unit 106 also determines a general dependence of attenuation as a function of wavelength by measuring attenuations in two or more predetermined separate optical bands 206, 208 apart from the predetermined bands associated with the lignin and the dry matter.

The attenuation of a measured band $\Delta\lambda i$, where i refers to an index of a band and $\Delta\lambda$ refers to a wavelength range in the band i, may be measured on the basis of the optical power $I_{\Delta\lambda,i}$ received by the detector 104. In an embodiment, the attenuation of a measured band $\Delta\lambda i$, may be measured by comparing the optical power $I_{0,\Delta\lambda,i}$ directed to the measured sheet 100 and the optical power $I_{\Delta\lambda,i}$ received by the detector 104. A measured band $\Delta\lambda i$ may comprise monochromatic optical radiation or a continuous wavelength range. Attenuation $A_i$, which may be interpreted as absorbance, in each optical band i may then be determined as:

$$A_i = -\log(I_{\Delta\lambda,i}/I_{0,\Delta\lambda,i}).$$

More accurately the attenuation $A_i$ may be solved from an equation $I_{\Delta\lambda,i} = I_{0,\Delta\lambda,i} \exp(-(\sum_{j=1}^{N} as_j + \sum_{j=1}^{N} aa_j)x)$, where exp is an exponential function based on Euler's number (about 2.71828) or 10, for example, j is the index of an substance in the measured sheet 100, N is the number of substances, $as_j$ is a scattering coefficient, $aa_j$ is an absorption coefficient and x is a traveled distance of the optical radiation in the measured sheet 100. The coefficients $as_j$ and $aa_j$, depend on a concentration of the substance j. Since the distance x may be ignored, the measured attenuation $A_1$ is a function of the sum of the scattering coefficients $\sum_{j=1}^{N} as_j$ and the sum of absorption coefficients $\sum_{j=1}^{N} aa_j$, $A_i = -\log(I_{\Delta\lambda,i}/I_{0,\Delta\lambda,i}) = (\sum_{j=1}^{N} as_j + \sum_{j=1}^{N} aa_j)$ where the logarithmic function is based on Euler's number (about 2.71828) or 10, for example. The term $I_{0,\Delta\lambda,i}$ may often be ignored such that its value may be assumed as 1, for instance. In the measurement, attenuation of lignin may be measured. Additionally, an attenuation of cellulose material may be measured. However, other substances such as coloring materials cause a general wavelength dependence of the attenuation which may result in displacement and tilt of baseline attenuation. The coloring substance may be ink used to print readable characters such as alpha numeric signs and/or images on the sheet.

The attenuation may then be expressed as $A = (as_o + as_l + as_c + aa_o + aa_l + aa_c)$ where $as_o$ is a scattering coefficient of other substances, $as_l$ is a scattering coefficient of lignin, $as_c$ is a scattering coefficient of cellulose, $aa_o$ is an absorption coefficient of other substances, $aa_l$ is an absorption coefficient of lignin and $aa_c$ is an absorption coefficient of cellulose. Since the coefficients $as_o + as_l + as_c + aa_o + aa_l + aa_c$ are wavelength dependent, the derivative or difference quotient of the optical power as a function of wavelength depends on the scattering and absorption coefficients $as_o$ and $aa_o$, irrespective whether the rest of the coefficients $as_l$, $as_c$, $aa_l$ and $aa_c$ are constant or variable. The value of the scattering and absorption coefficients $as_o$ and $aa_o$ depends on the other substances in paper. This is why the measurement of paper comprising coloring substances or the like, such as ink, on the surface or inside the sheet may face problems. However, it is possible to determine the general dependence of attenuation with respect to wavelength caused by the other substances.

In an embodiment, the measuring unit 106 determines the general dependence of attenuation with respect to wavelength in the environment of the measured optical absorption bands 200, 202, 203, 204 of lignin and dry matter by measuring attenuations in the two or more predetermined separate optical bands 206, 208, 210, 212 apart from the predetermined optical absorption bands 200, 202, 203, 204 of lignin and dry matter. The general dependence of attenuation means a basic behavior of an attenuation curve 220 without absorption of the lignin and the dry matter such as cellulose. For example, if the measuring unit 106 measures the lignin dependent value in a band 200 and the dry matter dependent value in a band 204, the measurement unit 106 may measure the attenuations taking into account the other substance(s) in three separate optical bands 206, 208 and 210. The optical band 200 may comprise wavelength 1660 nm (6000.0 cm$^{-1}$), the optical band 204 may comprise wavelength 2100 nm (4760 cm$^{-1}$), the optical band 206 may comprise wavelength 2250 nm (4440 cm$^{-1}$), the optical band 208 may comprise wavelength 5500 nm (1820 cm$^{-1}$) and the optical band 210 may comprise wavelength 1560 nm (6400 cm$^{-1}$). For measuring the environment of the maximum lignin absorbance in a band comprising wavelength 1450 nm (6900 cm$^{-1}$) a separate band 212 having wavelength 1300 nm (7690 cm$^{-1}$) apart from the predetermined optical absorption bands 200, 202, 203, 204 of lignin and dry matter may also be measured.

The measuring unit 106 may determine the general dependence of attenuation with respect to wavelength as a desired type of function the parameters of which are based on the attenuation values in the measured optical bands 206, 208, 210, 212 apart from the predetermined optical absorption bands 200, 202, 203, 204 related to lignin or lignin and dry matter. In an embodiment, the type of function may be a linear function $A_c = b\lambda + c$, where $A_c$ is attenuation associated with other substances in the sheet, $\lambda$ is a wavelength, b is a first parameter and c is a second parameter. The parameters b and c may be determined by requiring the linear function (=straight baseline) 216 pass through the measured points in optical bands 212 and 210 outside the absorption bands of lignin. According to another example, the parameters b and c may be determined by requiring the linear function (=straight baseline) 218 pass through the measured points in optical bands 210 and 208 outside the absorption bands of lignin. According to a further example, the parameters b and c may be determined by requiring the linear function (=straight baseline) 222 pass through the measured points in optical bands 208 and 206 outside the absorption bands of dry matter.

In an embodiment, the baseline of the general dependence of attenuation may comprise a piecewise linear function formed from at least two linear functions. In such a case, the curve of the general dependence of attenuation may be continuous but the slope may vary in different pieces.

In an embodiment, the type of function may also be a non-linear elementary or non-elementary function $f(\lambda)$. An example of non-linear elementary function is a polynomial function the degree of which is different from 1 and 0. In a similar manner, any function $f(\lambda)$ may be required to pass through the at least two measured points 206, 208, 210, 212. The bandwidth of the measured bands may vary from about 1 nm to 100 nm, for instance.

The measuring unit 106 may measure the general dependence of attenuation on the basis of at least two optical bands. One band 206 may be such that each of its wavelengths is longer than any of the wavelengths of the predetermined optical absorption bands 200 to 204 of lignin and dry matter. At least one band 208, 210 may be such that each of its wavelengths is between a predetermined optical absorption band 202 (or 200 for band 208) of lignin and a predetermined optical absorption band 204 of dry matter. A third possible band 212 is such that each of its wavelengths is shorter than any of the wavelengths of predetermined optical absorption bands 200 to 204 of lignin and dry matter. The measurement may be performed in a similar manner in the bands 208, 200, 204 and 210.

The measuring unit 106 may form corrected lignin dependent value Alc by removing the general dependence of attenuation from the lignin dependent value Al. Correspondingly, the measuring unit 106 may form corrected dry matter dependent value Acc by removing the general dependence of attenuation from the dry matter dependent value Ac. A corrected lignin dependent value Alc may be integrated over a measured band $\lambda 1$ to $\lambda 2$, $Alc = \int_{\lambda 1}^{\lambda 2} (f_s(x) - f_d(x))dx$, where the optical absorption band 200 related to lignin is from $\lambda 1$ to $\lambda 2$, $f_s(x)$ is the optical attenuation distribution in the optical band 200, $f_d(x)$ is the desired function determined by values at the measured bands 212 and 210 or 210 and 208 or 208 and 206, for example. A corrected dry matter dependent value Acc may be expressed in a mathematical form as $Acc = \int_{\lambda 1}^{\lambda 2} (f_s(x) - f_d(x))dx$, where the optical band 206 related to dry matter is from λ1 to λ2, $f_s(x)$ is the optical attenuation distribution in the optical band 204, $f_d(x)$ is the desired function determined by values at the measured bands 208 and 206.

Figure 3:
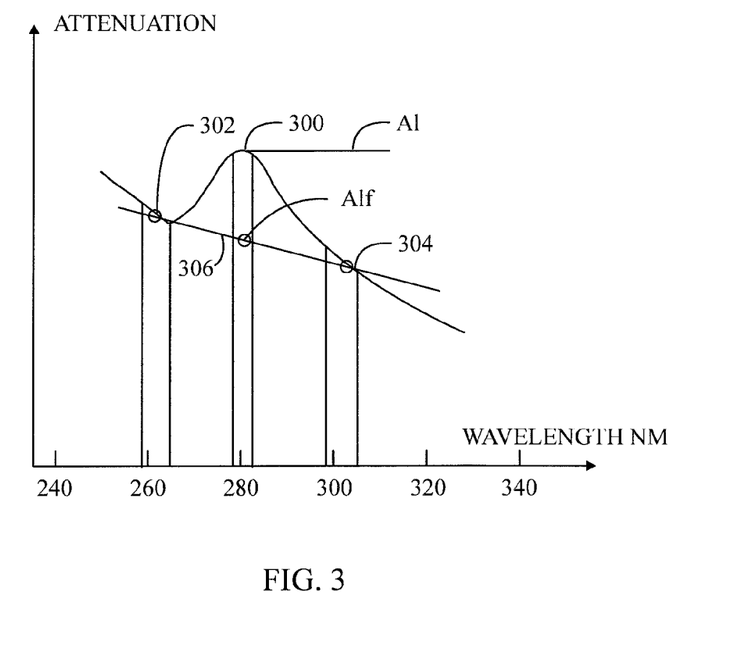
FIG. 3 shows a measurement in ultraviolet light.

In an embodiment, the measuring unit 106 may form each corrected lignin value Alc as a difference between a corresponding value Alf formed on the basis of the known type of function for a predetermined optical absorption band 200, 202, 203, 204 of lignin and a corresponding lignin dependent value Al. The value Alf may be formed by setting the optical band 200, 202, 203, 204 as an argument for the known type of function, $f(\Delta\lambda_k)=Alf_k$, where k is an index of the predetermined optical absorption band. In an embodiment, the measuring unit 106 may form each corrected dry matter value Acc as a difference between a value Acf formed on the basis of the known type of function for a predetermined optical absorption band 204 of the dry matter absorption and a corresponding dry matter dependent value Ac. In a mathematical form the corrected lignin value Alc may be expressed as Alc=Al−Alf. In a mathematical form the corrected dry matter value Acc may be expressed as Acc=Ac−Acf. FIG. 3 presents a measurement of a sample containing lignin in ultraviolet light. The y-axis is attenuation in an arbitrary scale, and the x-axis is wavelength in nanometers. The lignin dependent value Al may be measured in a predetermined optical absorption band 300 of lignin. The optical band 300 may comprise a wavelength about 280 nm ($35714$ cm$^{-1}$) and the optical bandwidth may range from sub-nanometers to tens of nanometers, for example. The general dependence of attenuation as a function of wavelength may be measured at both sides of the maximum lignin absorption without including the optical absorption band 300 of lignin. A first optical band 302 apart from the maximum lignin absorption band may comprise a wavelength about 265 nm, for instance. A second optical band 304 apart from the maximum lignin absorption band may comprise a wavelength about 300 nm, for instance.

The measuring unit 106 may determine the general dependence of attenuation with respect to wavelength as a desired type of function the parameters of which are based on the attenuation values in the measured wavelength bands 302, 304 apart from the predetermined absorption band 300 related to lignin. In an embodiment, the type of function may be a linear function $A_c=b\lambda+c$, where $A_c$ is attenuation associated with other substances such as coloring substances, λ is a wavelength, b is a first parameter and c is a second parameter. The parameters b and c may be determined by requiring the linear function (=straight baseline) 306 pass through the measured points in optical bands 302 and 304 outside the attenuation band of lignin.

Correspondingly as explained earlier, the measuring unit 106 may form a corrected lignin value Alc as a difference between a corresponding value Alf formed on the basis of the known type of function for a predetermined optical absorption band 300 of lignin and a corresponding lignin dependent value Al. In a mathematical form, the corrected lignin value Alc may be expressed as Alc=Al−Alf.

For example, Alf for the optical band 202 may be computed as Alf (202)=(a1+r(a2−a1)), where Alf(202) refers to Alf in the optical band 202, k is a coefficient, a1 is the value of attenuation in the band 212 and a2 is the attenuation in the band 210. The coefficient r may be a ratio I/L of distance I between the optical bands 212 and 202 and distance L between the optical bands 212 and 210. In other cases, Alf and Acc may be computed in a similar manner.

In an embodiment, the dry matter content may be formed by giving coefficients to the measurements in different optical bands. Hence, the value representing dry matter content may be formed on the basis of the at least one lignin dependent value, the at least one dry matter dependent value, and the general dependence of attenuation. An algorithm having coefficients for different measured values may be as follows:

$$X=(a_0+a_1A_1+a_2A_2+a_3A_3+a_4A_4)/(b_0+b_1A_1+b_2A_2+b_3A_3+b_4A_4),$$

where $A_1$ refers to a measurement of general dependence, $A_2$ refers to a measurement in an optical band associated with a lignin absorption peak, $A_3$ refers to a measurement in an optical band associated with a dry matter absorption peak and $A_4$ refers to a measurement of general dependence. $A_1$ may be measured at about 1820 nm (208), $A_2$ may be measured at about 2175 nm (203), $A_3$ may be measured at about 2100 nm (204) and $A_4$ may be measured at 2250 nm (206). The numerator may be interpreted to represent a corrected lignin dependent value and the denominator may be interpreted to represent a corrected dry matter dependent value. The coefficients $a_0$, $a_1$, $a_2$, $a_3$, $a_4$ and $b_0$, $b_1$, $b_2$, $b_3$, $b_4$ may be determined on the basis of test measurements with predetermined samples, for example. In general, the variable X may have at least two terms in the numerator and in the denominator: $X=(a_0+\ldots+a_NA_N)/(b_0+\ldots+b_NA_N)$, where N is the number of the terms and N is at least 1. The variable X may be the dry matter content directly.

However in an embodiment, the variable X and values of measured reference samples of predetermined lignin content may be matched together using a polynomial fitting. The number of coefficients $d_0\ldots d_M$ depends on the degree M of the fitting polynomial which may be at least one. The coefficients $d_0\ldots d_M$, in turn, may be determined on the basis of test measurements of predetermined samples. The degree of the polynomial may be 2, for example. Then the value representing a dry matter value DRY may be computed to be: $DRY=d_0+d_1X+d_2X^2$.

Figure 4A:
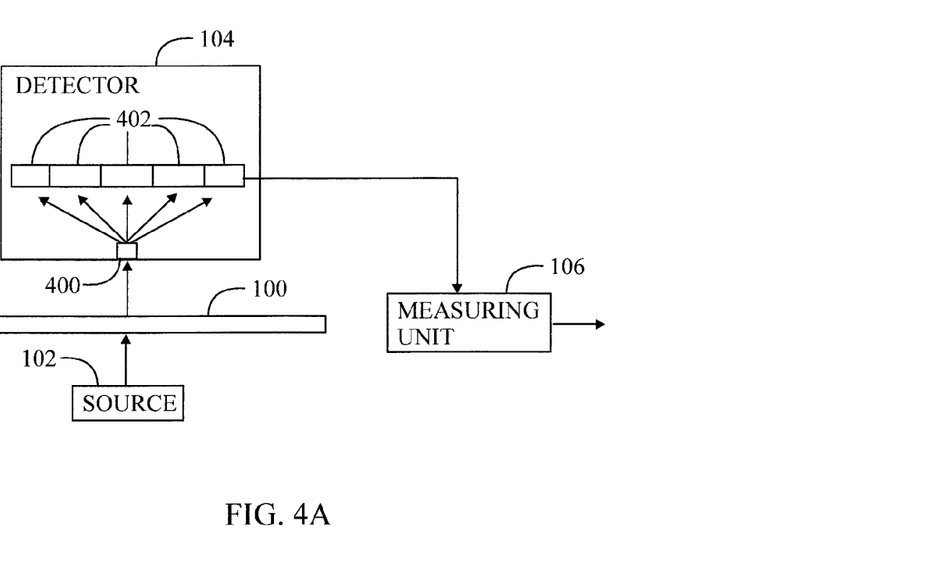
FIG. 4A shows a measuring system with a dispersing element.

FIG. 4A presents an embodiment where the detector 104 may comprise a dispersing component 400 which disperses the optical radiation into a spectrum of different optical bands Δλ1 to ΔλM and a plurality of detector elements 402. The dispersing component 400 may comprise a prism or an optical grating. The detector 104 may comprise a spectrometer. The detector elements 402 may form an array or a matrix. Each of the detector elements 402 receives one of the optical bands of the dispersed optical radiation and is responsive thereto by outputting an electrical signal corresponding to an optical power of the optical band. The electrical signals may be fed to the measuring unit 106. An electrical signal from a suitable detector element 402 may alone be a signal relating to data on attenuation in a measured band. Alternatively, signals from a plurality of detector elements 402 may comprise information on one measured optical band.

Figure 4B:
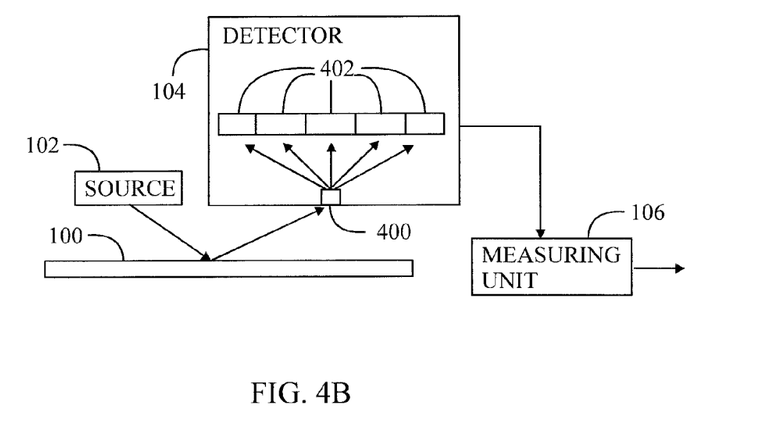
FIG. 4B shows a measuring system with a dispersing element for the reflected light.

FIG. 4B presents an embodiment where the measurement of FIG. 4A is performed using reflected optical radiation from the object 100.

Figure 5:
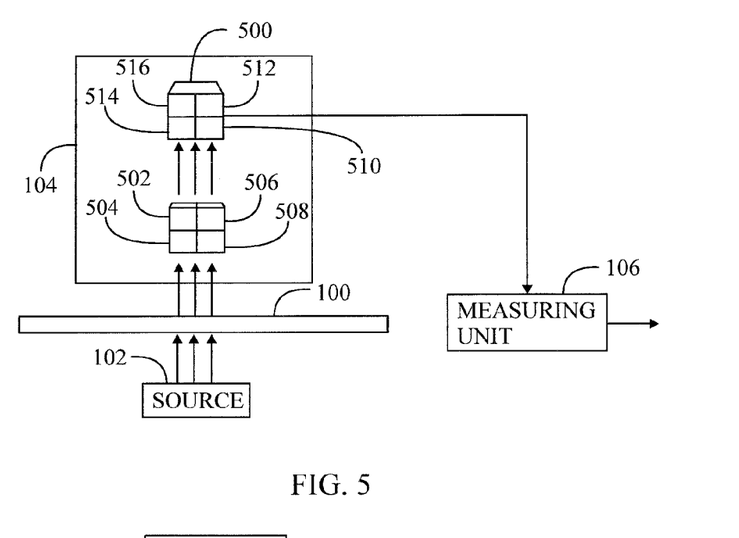
FIG. 5 shows a measuring system comprising a multi-channel detector with interference filters.

FIG. 5 presents an embodiment where the detector 104 may comprise a multichannel detector 500 and an optical interference filter 502, 504, 506, 508 for each channel 510, 512, 514, 516 of the multichannel detector 500. The number of channels is at least three for the lignin measurement and four for the dry matter measurement. At least one optical interference filter 502 may have one or more predetermined optical pass bands 200, 202, 203, 300 associated with absorption of lignin. Each of at least two optical interference filters 506, 508 may have a predetermined separate optical pass band 206, 208, 210, 212, 302, 304 apart from the predetermined optical absorption bands 200, 202, 203, 300 of lignin.

At least one optical interference filter 504 may have one or more predetermined optical pass bands 204 associated with absorption of the dry matter. At least one optical interference filter 506 may have one or more predetermined separate optical pass bands 206, 208, 210, 212, 302, 304 apart from the predetermined optical absorption bands 200, 202, 203, 204, 300 of lignin and the dry matter. At least one further optical interference filter 508 may also have one or more predetermined separate optical pass bands 206, 208, 210, 212, 302, 304 apart from the predetermined optical absorption bands 200, 202, 203, 204, 300 of lignin and the dry matter. At least one optical pass band of the interference filter 508 is different from the at least one pass band of the interference filter 506. The channels 510 to 516 may feed their responses to the measuring unit 106 which processes the detected optical bands as described above.

A typical bandwidth Δλ of a pass band of an interference filter is between 1 nm to 100 nm, for example. The bandwidth may be selected freely. A middle wavelength of the pass band may be adjusted freely such that a suitable measured optical band may be passed to the detector 104.

Figure 6:
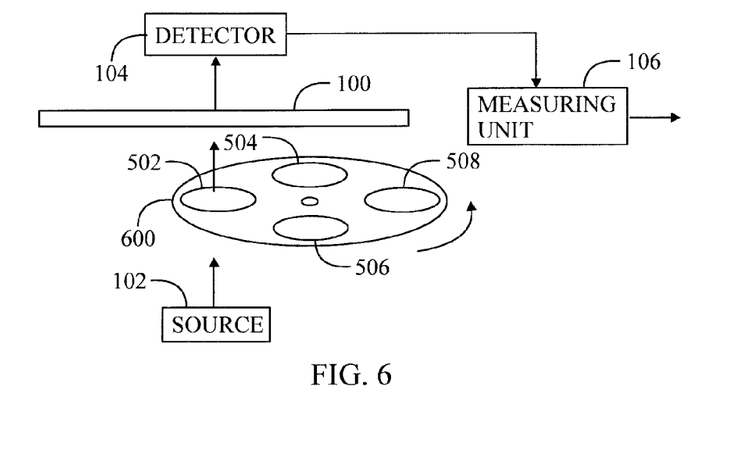
FIG. 6 shows a measuring system with revolving interference filters.

FIG. 6 presents an embodiment which utilizes a revolving interference filter disc 600. The optical source is a broad band optical source capable of outputting all measured bands of optical radiation. The detector 104 is capable of outputting an electrical signal relative to an optical power it receives. The disc 600 may have at least four interference filters 502, 504, 506, 508 each of which is capable of passing one measured optical band through. The filters have been explained in the explanation of FIG. 5. When the disc 600 is rotating, the interference filters 502, 504, 506, 508 pass the measured optical bands towards the measured sheet 100 one after another. The detector 104 correspondingly detects the measured optical bands one after another. Electrical signals related to the detected optical bands may be fed to the measuring unit 106 which processes the detected optical bands as described above.

Figure 7:
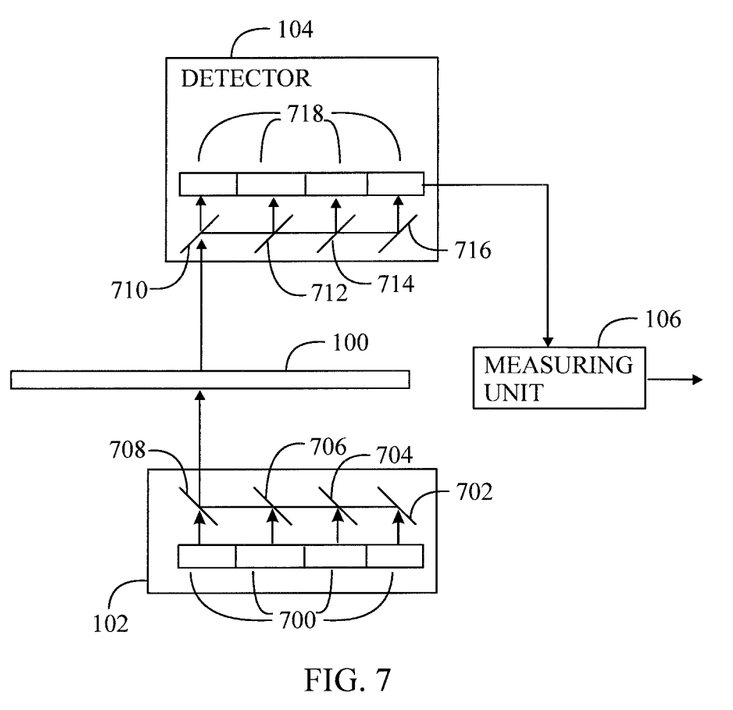
FIG. 7 shows a measuring system with a plurality of narrow band optical sources and detection utilizing beam splitters.

FIG. 7 illustrates an embodiment which utilizes a group of optical source elements 700 which have a narrow optical output band. The optical source elements 700 may be lasers or LEDs having the wavelengths used in the measurement. The optical source 106 may have a reflector 702 such as a mirror for one optical source element in periphery, and beam splitters 704, 706, 708 for the rest of the optical source elements 700. The beam splitters 704 to 708 function as beam combiners such that all optical bands from the different optical source elements 700 are directed to the same section of the measured sheet 100. For a lignin measurement, two beam splitters and a reflector may be needed as a minimum requirement. For measuring both lignin and cellulose three beam splitters and a reflector may be needed as a minimum requirement.

The detector 106 may have a group of detector elements 718 and a reflector 716 such as a mirror for one optical detector element in periphery, and beam splitters 710, 712, 714 for the rest of the optical detector elements 718. The beam splitters 710 to 714 split the measured beam into different measured optical bands and direct each band to one detector element 718. For a lignin measurement, three detector elements, two beam splitters and a reflector may be needed as a minimum requirement. For measuring both lignin and the dry matter four detector elements, three beam splitters and a reflector may be needed as a minimum requirement.

Instead of a plurality of narrow band optical sources a broadband optical source may be used. If a broadband optical source is used, the mirror 702 and the beam splitters 704 to 708 may not be needed. Still, the detector 104 may remain the same as in FIG. 6.

If a plurality of narrow band optical sources 700 are used like in FIG. 6, the detector 104 may be similar to that presented in FIG. 3, i.e. the detector 104 comprises a spectrometer.

In an embodiment, at least one optical source may sweep over at least one measured wavelength band.

Figure 8:
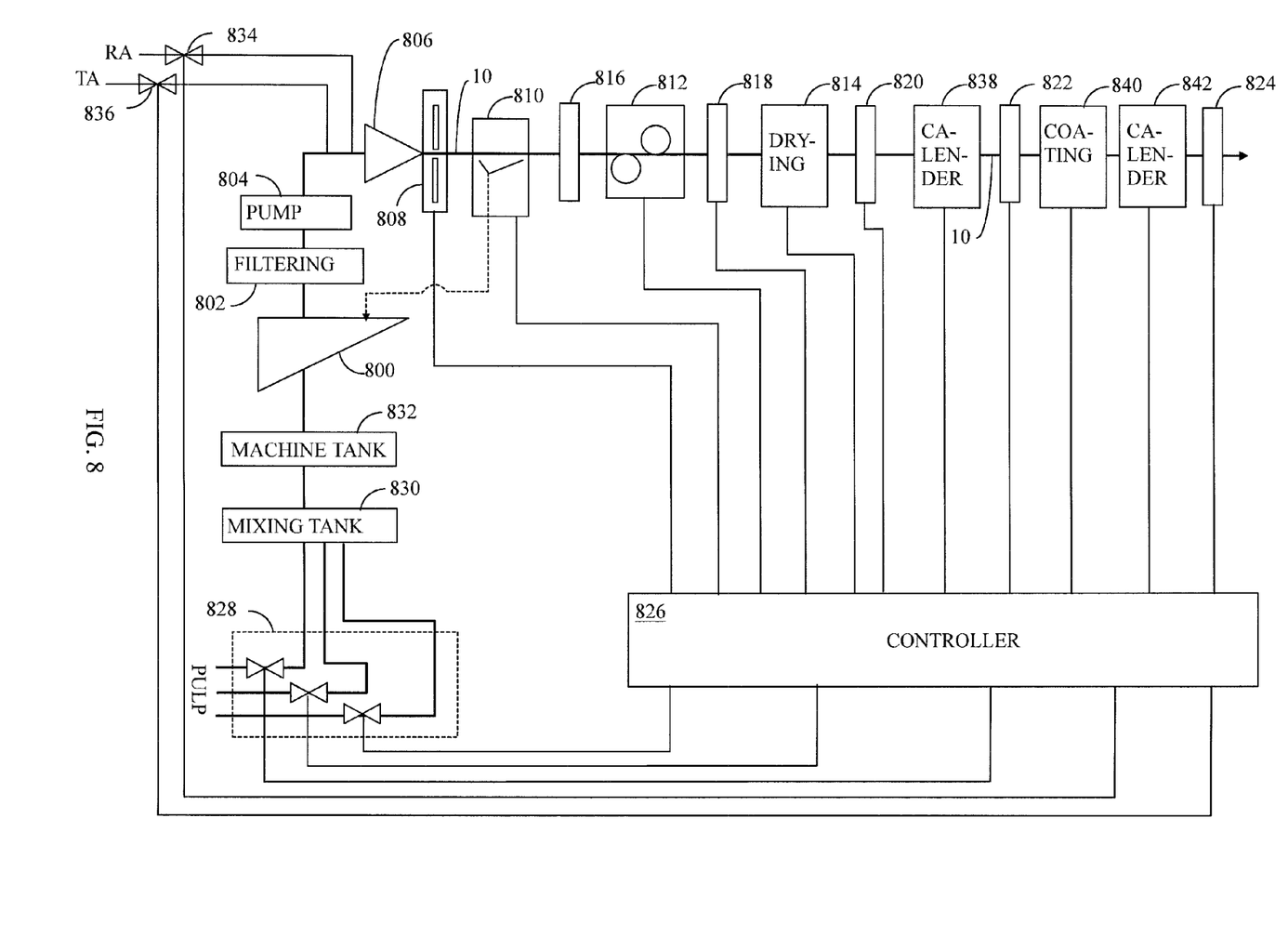
FIG. 8 illustrates a paper machine.

FIG. 8 shows the principle structure of a paper machine. A pulp flow or a plurality of pulp flows may be fed into the paper machine through a wire pit 800, which is usually preceded by a mixing tank 830 for pulp flows and a machine tank 832. The pulp may contain recycled paper. Machine pulp is batched for a short circulation by a weight control or a grade change program. The mixing tank 830 and the machine tank 832 may also be replaced by a separate mixing reactor (not shown in FIG. 8) and the batching of machine pulp is controlled by feeding each pulp flow separately by means of valves or some other flow regulating means 828. In the wire pit 800, the machine pulp is mixed with water to provide the short circulation (a broken line from a former 810 to the wire pit 800) with a desired consistency. From the pulp thus produced, it is possible to remove sand (hydrocyclones), air (deaeration tank) or other rough material (pressure screen) by cleaning equipment 802, and pulp is pumped by means of a pump 804 into a head box 806. Before the head box 806, if desired, a filler TA, such as kaolin clay, calcium carbonate, talc, chalk, titanium oxide, silica, etc., and/or a retention agent RA, such as inorganic, natural organic or synthetic water-soluble organic polymers may be added to the pulp. The TA and the RA belong to the dry matter in the sheet and the substances in them may be measured individually or in desired combinations with or without cellulose. The filler may be used to improve formation, surface properties, opacity, brightness and printability and to reduce manufacturing costs. The retention agents RA, for their part, increase the retention of fines and fillers and simultaneously speed up the dewatering in a manner known per se. Both the fillers and the retention agents thus affect the surface topography of the web and the paper.

From the head box 806, the pulp is fed through a slice 808 of the head box into the former 810, which may be a fourdrinier or a gap former. In the former 810, the web 10 is dewatered and ash, fines and fibres are removed into the short circulation. In the former 810, the pulp is fed as a web 10 onto the wire, and the web 10 is preliminarily dried and pressed in a press 812. The web 10 is primarily dried in a drying section 814. There is usually at least one measuring part 816, 818, 820, 822, 824, by which the lignin content and dry matter content of the web 10 can be measured.

A paper machine, which in this application refers to both paper and cardboard machines and also to pulp manufacturing machines, may also comprise, for instance, a precalender 838, a coating part/section 840 and/or a post-calender 842. However, there is not necessarily any coating section 840, and in that case there are not necessarily more than one calender 838, 842. In the coating section 840, a coating colour, which may contain for example kaolin, chalk or carbonate, starch, and/or latex, may be applied onto the paper surface. The use of coating colour usually reduces the roughness of the paper and improves glossiness.

In the calenders 838, 842, in which an uncoated or coated paper web travels between rolls that press with a desired force, the surface topography of the paper, such as roughness, can be changed. The calender 838, 842 may also affect the thickness and/or gloss of the paper. In the calender 838, 842, the properties of the paper web may be changed by moistening the web or by means of temperature and nip load/pressure between the rolls so that the greater the press applied to the web is, the smoother and glossier the paper will become. Moistening and an increase in the temperature further reduce roughness and improve glossiness. In addition, it is obvious that the operation of a paper machine is known per se to a person skilled in the art, wherefore it is not described in more detail in this context.

FIG. 8 also shows a control system for the paper machine. Factors affecting the quality and grade change include the amount and ratio of pulp flows, amount of filler, amount of retention agent, machine velocity, amount of backwater and drying capacity. A controller 826 may control at least one regulating unit which may regulate at least one property of the sheet one of which may be dry matter content. The controller 826 may control the batching of pulp flows by means of valves 828, the batching of the filler TA by a valve 836, the batching of the retention agent RA by a valve 834, feed of different pulp by the regulating means 828. The controller 826 may also control the size of the slice 808, the motor moving the sheet with the machine velocity, the valves regulating the amount of backwater and the drying process in block 814. The controller 826 utilizes the measuring devices 816 to 824 which comprise the detector 104 and usually also the optical radiation source 102 for monitoring moisture. The controller 826 may also measure the web 10 properties elsewhere (e.g. at the same points where controls are carried out).

The controller 826 may be considered as a control arrangement based on automatic data processing of the paper machine, or as a part thereof. The controller 826 may receive digital signals or convert the received analog signals to digital signals. The controller 826 may comprise a microprocessor and memory and process the signal according to a suitable computer program. The controller 826 may be based on a PID (Proportional-IntegralDerivative), MPC (Model Predictive Control) or GPC (General Predictive Control) control, for example.

Figure 9:
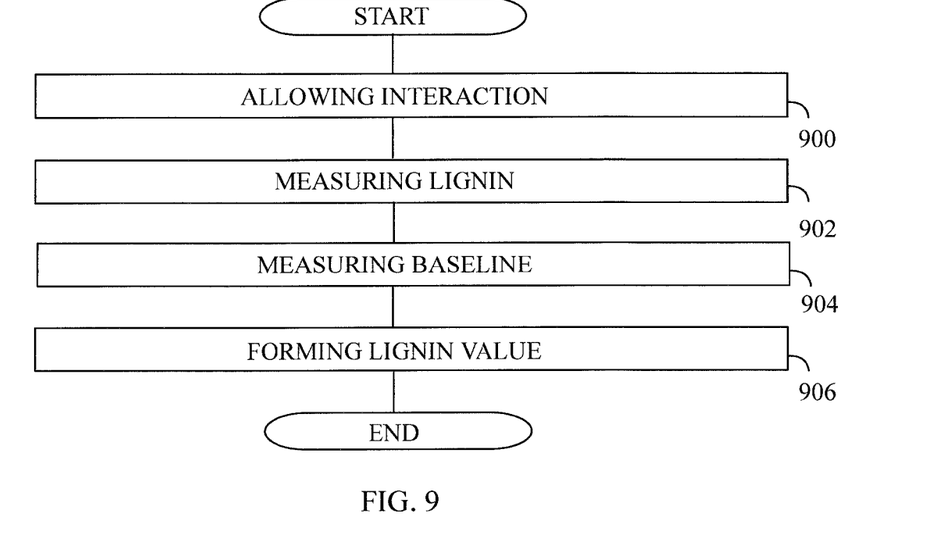
FIG. 9 shows a flow chart of the lignin measurement.

FIG. 9 presents a flow chart of the lignin measurement. In step 900, optical radiation is allowed to interact with a measured sheet comprising cellulose material and potentially lignin. In step 902, at least one lignin dependent value is measured on the basis of attenuation of the optical radiation interacted with the measured sheet at one or more predetermined optical absorption bands of lignin. In step 904, a general dependence of attenuation of the optical radiation interacted with the measured sheet with respect to wavelength is determined by measuring attenuations in two or more predetermined separate optical bands apart from the one or more predetermined optical absorption bands of lignin. In step 906, a value representing lignin content is formed by removing the determined general dependence of attenuation from the at least one lignin dependent value.

Figure 10:
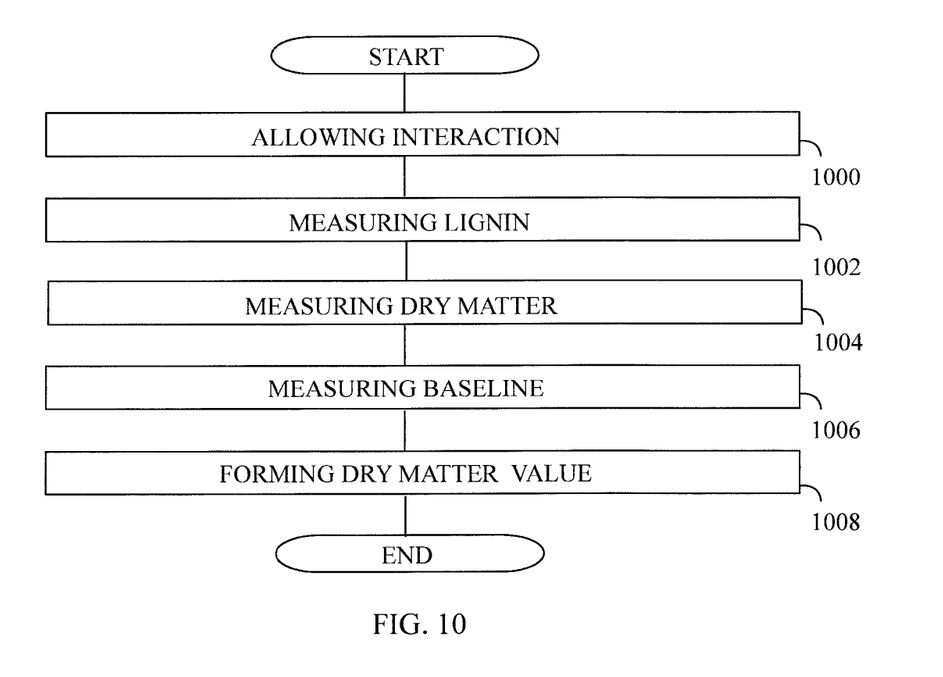
FIG. 10 presents a flow chart of dry matter measurement.

FIG. 10 presents a flow chart of dry matter measurement. In step 1000 optical radiation is allowed to interact with a measured sheet comprising dry matter and potentially lignin. In step 1002, at least one lignin dependent value is measured on the basis of attenuation of the optical radiation interacted with the measured sheet in one or more predetermined optical absorption bands of lignin. In step 1004, at least one dry matter dependent value is measured on the basis of attenuation of the optical radiation interacted with the measured sheet in one or more predetermined optical absorption bands of the dry matter. In step 1006, a general dependence of attenuation of the optical radiation interacted with the measured sheet with respect to wavelength is determined by measuring attenuations at two or more predetermined separate optical bands apart from the predetermined optical absorption bands of lignin and the dry matter. In step 1008, a value representing a dry matter content is formed on the basis of the at least one lignin dependent value, the at least one dry matter dependent value and the general dependence of attenuation.

Figure 11:
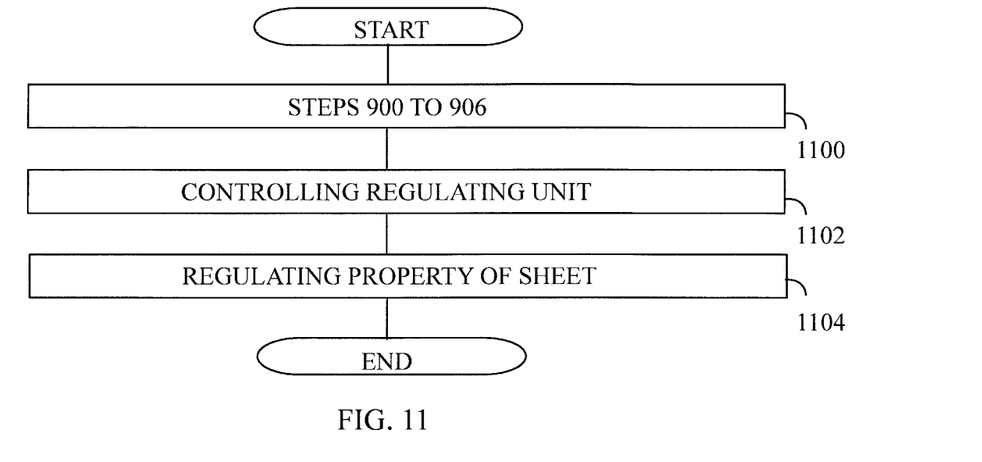
FIG. 11 shows a flow chart of a control method based on the lignin content of the sheet.

FIG. 11 present a flow chart of a control method based on the lignin content of the sheet. The method step 1100 comprises the steps of FIG. 9 and further comprises step 1102 where at least one regulating unit is controlled on the basis of the measured lignin content. In step 1104, the at least one regulating unit regulates at least one property of the measured sheet on the basis of control.

Figure 12:
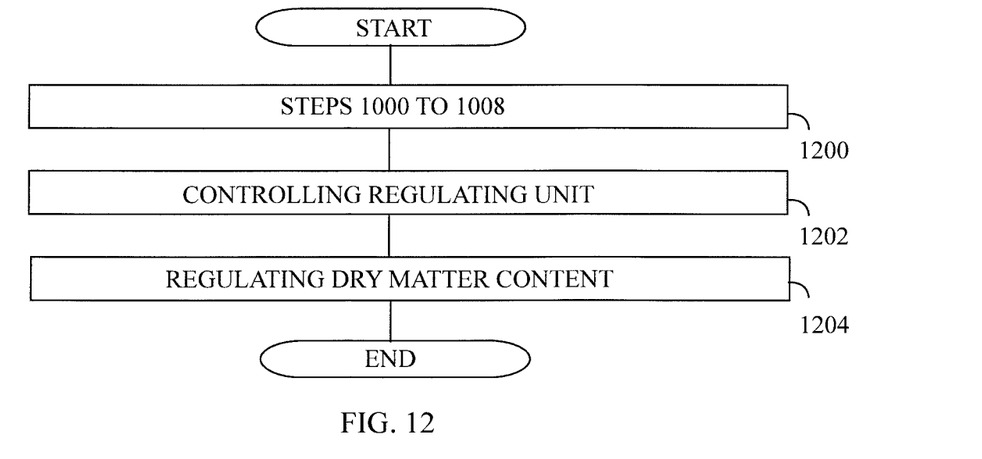
FIG. 12 present a flow chart of a control method based on the dry matter content of the sheet.

FIG. 12 present a flow chart of a control method based on the dry matter content of the sheet. The method step 1200 comprises the steps of FIG. 10 and further comprises step 1202 where at least one regulating unit is controlled on the basis of the measured dry matter content. In step 1204, the at least one regulating unit regulates the dry matter content in the measured sheet on the basis of control.

The measuring unit 106 and the controllers 700, 826 capable of performing the steps presented in at least one of FIGS. 9 and 10 may be implemented as an electronic digital computer, or a circuitry which may comprise a working memory (RAM), a central processing unit (CPU), and a system clock. The CPU may comprise a set of registers, an arithmetic logic unit, and a controller. The controller or the circuitry is controlled by a sequence of program instructions transferred to the CPU from the RAM. The controller may contain a number of microinstructions for basic operations. The implementation of microinstructions may vary depending on the CPU design. The program instructions may be coded by a programming language, which may be a high-level programming language, such as C, Java, etc., or a low-level programming language, such as a machine language, or an assembler. The electronic digital computer may also have an operating system, which may provide system services to a computer program written with the program instructions.

The measuring unit 106 and the controllers 700, 826 may comprise circuitries which refer to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present.

As a further example, the term 'circuitry' would also cover an implementation of merely a processor (or multiple processors) or a portion of a processor and its (or their) accompanying software and/or firmware.

An embodiment provides a computer program embodied on a distribution medium, comprising program instructions which, when loaded into an electronic apparatus, are configured to control the apparatus to execute the embodiments described above.

The computer program may be in source code form, object code form, or in some intermediate form, and it may be stored in some sort of carrier, which may be any entity or device capable of carrying the program. Such carriers include a record medium, computer memory, read-only memory, and a software distribution package, for example. Depending on the processing power needed, the computer program may be executed in a single electronic digital computer or it may be distributed amongst a number of computers.

The apparatuses may also be implemented as one or more integrated circuits, such as application-specific integrated circuits ASIC (Application Specific Integrated Circuit). Other hardware embodiments are also feasible, such as a circuit built of separate logic components. A hybrid of these different implementations is also feasible. When selecting the method of implementation, a person skilled in the art will consider the requirements set for the size and power consumption of the apparatus, the necessary processing capacity, production costs, and production volumes, for example.

It will be obvious to a person skilled in the art that, as technology advances, the inventive concept can be implemented in various ways. The invention and its embodiments are not limited to the examples described above but may vary within the scope of the claims.

The invention claimed is:

1. An apparatus for measuring a sheet comprising cellulose material and potentially lignin, the apparatus comprising:
   a detector configured to receive optical radiation transmitted through the measured sheet and being responsive to one or more predetermined optical absorption bands of lignin, and two or more separate optical bands apart from the one or more predetermined optical absorption bands of the lignin; and
   a measuring unit configured to, on the basis of responses of the detector:
      measure at least one lignin dependent value on the basis of attenuation of the optical radiation of ultraviolet light or infrared region in the one or more predetermined optical absorption bands of lignin,
      determine a general dependence of attenuation with respect to wavelength as a known type of function the parameters of which are based on the attenuation values at the measured wavelengths apart from the predetermined absorption bands of lignin, the two or more separate optical bands apart from the one or more predetermined optical absorption bands of the lignin fulfilling at least two of the following: a band each wavelength of which being longer than any of the wavelengths of the predetermined optical absorption bands of lignin, and a band each wavelength of which being shorter than any of the wavelengths of predetermined optical absorption bands of lignin, and
      form a value representing lignin content by removal of the general dependence of attenuation from the at least one lignin dependent value by forming each value of lignin content as a difference between corresponding values of the general dependence of attenuation and the lignin dependent value.

2. An apparatus for measuring a sheet comprising cellulose material and potentially lignin, the apparatus comprising:
   a detector configured to receive optical radiation transmitted through the measured sheet and being responsive to one or more predetermined optical absorption bands of lignin, one or more predetermined optical absorption bands of dry matter and two or more separate optical bands apart from the predetermined optical absorption bands of the lignin and the dry matter; and
   a measuring unit configured to, on the basis of responses of the detector:
      measure at least one lignin dependent value on the basis of attenuation of the optical radiation of ultraviolet light or infrared region in the one or more predetermined optical absorption bands of lignin,
      measure at least one dry matter dependent value on the basis of attenuation of the optical radiation in the one or more predetermined optical absorption bands of the dry matter,
      determine a general dependence of attenuation with respect to wavelength as a known type of function the parameters of which are based on the attenuation values at the measured wavelengths apart from the predetermined absorption bands of lignin and the dry matter, two or more predetermined optical bands apart from the predetermined absorption bands of lignin and dry matter fulfilling at least two of the following: a band each wavelength of which being longer than any of the wavelengths of the predetermined optical absorption bands of lignin and the dry matter, a band each wavelength of which being between one of the predetermined optical absorption bands of lignin and the dry matter, and a band each wavelength of which being shorter than any of the wavelengths of predetermined optical absorption bands of lignin and the dry matter, and
      form a value representing a dry matter content on the basis of the at least one lignin dependent value, the at least one dry matter dependent value and the general dependence of attenuation.

3. The apparatus of claim 2, the measuring unit being configured to form corrected lignin and dry matter dependent values by removing the general dependence of attenuation from the lignin and dry matter dependent values, and
   form a value representing a dry matter content on the basis of the at least one corrected lignin dependent value and the at least one corrected dry matter dependent value.

4. The apparatus of claim 1, the apparatus comprising an optical source configured to output the optical radiation for transmission through the measured object.

5. The apparatus of claim 1, wherein the detector comprising a plurality of detector elements and a dispersing component configured to disperse the optical radiation into optical bands comprising the measured optical bands, and the detector elements being configured to receive the optical bands and being responsive thereto.

6. The apparatus of claim 1, wherein the detector comprising a multichannel detector with at least three channels and an optical interference filter for each channel of the detector; the at least three optical interference filters having one or more predetermined optical pass bands associated with absorption of lignin, and two or more separate optical pass bands apart from the predetermined optical bands associated with absorption of lignin; and the channels of the detector being configured to feed their responses to the measuring unit.

7. The apparatus of claim 2, wherein the detector comprising a multichannel detector with at least four channels and an optical interference filter for each channel of the detector; the at least four optical interference filters having one or more predetermined optical pass bands associated with absorption of lignin, one or more predetermined optical pass bands associated with absorption of dry matter and two or more separate optical pass bands apart from the predetermined optical bands; and the channels of the detector being configured to feed their responses to the measuring unit.

8. A system, comprising the apparatus of claim 1, wherein the system comprising at least one regulating unit and a controller, the at least one regulating unit being configured to regulate at least one property of the measured sheet and the controller being configured to control the at least one regulating unit on the basis of the measured lignin content.

9. A system, comprising the apparatus of claim 2, wherein the system comprising at least one regulating unit and a controller, the at least one regulating unit being configured to regulate the dry matter content in the measured sheet and the controller being configured to control the at least one regulating unit on the basis of the measured dry matter content.

10. A method for measuring a sheet comprising cellulose material and potentially lignin, the method comprising:
  allowing optical radiation to interact with the measured sheet;
  measuring at least one lignin dependent value on the basis of attenuation of the optical radiation of ultraviolet light or infrared region transmitted through the measured sheet in one or more predetermined optical absorption bands of lignin;
  determining, by the measuring unit, a general dependence of attenuation with respect to wavelength as a known type of function the parameters of which are based on the attenuation values at the measured wavelengths apart from the predetermined absorption bands associated with lignin, two or more separate optical bands apart from the one or more predetermined optical absorption bands of the lignin fulfilling at least two of the following: a band each wavelength of which being longer than any of the wavelengths of the predetermined optical absorption bands of lignin, and a band each wavelength of which being shorter than any of the wavelengths of predetermined optical absorption bands of lignin; and
  forming a value representing lignin content by cancelling the determined general dependence of attenuation from the at least one lignin dependent value by forming each value of lignin content as a difference between corresponding values of the general dependence of attenuation and the lignin dependent value.

11. A method for measuring a sheet comprising cellulose material and potentially lignin, the method comprising:
  allowing optical radiation to interact with the measured sheet;
  measuring at least one lignin dependent value on the basis of attenuation of the optical radiation of ultraviolet light or infrared region transmitted through the measured sheet in one or more predetermined optical absorption bands of lignin;
  measuring at least one dry matter dependent value on the basis of attenuation of the optical radiation interacted with the measured sheet in one or more predetermined optical absorption bands of dry matter;
  determining, by a measuring unit, the general dependence of attenuation with respect to wavelength as a known type of function the parameters of which are based on the attenuation values at the measured wavelengths apart from the predetermined absorption bands associated with lignin and dry matter, two or more predetermined optical bands apart from the predetermined absorption bands of lignin and dry matter fulfilling at least two of the following: a band each wavelength of which being longer than any of the wavelengths of the predetermined optical absorption bands of lignin and the dry matter, a band each wavelength of which being between one of the predetermined optical absorption bands of lignin and the dry matter, and a band each wavelength of which being shorter than any of the wavelengths of predetermined optical absorption bands of lignin and the dry matter; and
  forming a value representing a dry matter content on the basis of the at least one lignin dependent value, the at least one dry matter dependent value and the general dependence of attenuation.

12. The method of claim 11, the method further comprising forming corrected lignin and dry matter dependent values by removing the determined general dependence of attenuation from the lignin and dry matter dependent values; and
  forming a value representing a dry matter content on the basis of the at least one corrected lignin dependent value and the at least one corrected dry matter dependent value.

13. The method of claim 10, the method further comprising determining, by the measuring unit, the general dependence of attenuation with respect to wavelength as a known type of function the parameters of which are based on the attenuation values at the measured wavelengths apart from the predetermined absorption bands associated with lignin; and forming each corrected lignin value as a difference between a lignin dependent value and a corresponding value formed on the basis of the known type of function for a predetermined optical absorption band of lignin.

14. The method of claim 10, the method further comprising dispersing, in the detector, the optical radiation into a spectrum, and receiving and responding to an optical band of the spectrum by each detector element.

15. The method of claim 10, wherein the detector comprising a multichannel detector and an optical interference filter for each channel of the detector; at least one optical interference filter having one or more predetermined optical pass bands associated with absorption of lignin, and two or more separate optical pass bands apart from the predetermined optical absorption bands of lignin; and feeding, by the channels, their responses to the measuring unit.

16. The method of claim 11, wherein the detector comprising a multichannel detector and an optical interference filter for each channel of the detector; at least one optical interference filter having one or more predetermined optical pass bands associated with absorption of lignin, one or more predetermined optical pass bands associated with absorption of dry matter and two or more separate optical pass bands apart from the predetermined optical absorption bands of lignin and dry matter; and feeding, by the channels, their responses to the measuring unit.

17. A method, the method comprising the steps of claim 10 and further comprising controlling at least one regulating unit on the basis of the measured lignin content, the at least one regulating unit regulating the at least one property of the measured sheet on the basis of the control.

18. A method, the method comprising the steps of claim 10 and further comprising controlling at least one regulating unit on the basis of the measured lignin content, the at least one regulating unit regulating the dry matter content in the measured sheet on the basis of the control.

19. An apparatus for measuring a sheet comprising cellulose material and potentially lignin, the apparatus comprising:
  at least one processor; and at least one memory including a computer program code, wherein the at least one memory and the computer program code are configured, with the at least one processor, to cause the apparatus at least to perform:

allowing optical radiation to interact with the measured sheet, measuring at least one lignin dependent value on the basis of attenuation of the optical radiation of ultraviolet light or infrared region transmitted through the measured sheet in one or more predetermined optical absorption bands of lignin, determining a general dependence of attenuation with respect to wavelength as a known type of function the parameters of which are based on the attenuation values at the measured wavelengths apart from the predetermined absorption bands of lignin, two or more separate optical bands apart from the one or more predetermined optical absorption bands of the lignin fulfilling at least two of the following: a band each wavelength of which being longer than any of the wavelengths of the predetermined optical absorption bands of lignin, and a band each wavelength of which being shorter than any of the wavelengths of predetermined optical absorption bands of lignin, forming a value representing lignin content by cancelling the determined general dependence of attenuation from the at least one lignin dependent value by forming each value of lignin content as a difference between corresponding values of the general dependence of attenuation and the lignin dependent value.

20. An apparatus for measuring a sheet comprising cellulose material and potentially lignin, the apparatus comprising:

at least one processor; and at least one memory including a computer program code, wherein the at least one memory and the computer program code are configured, with the at least one processor, to cause the apparatus at least to perform:

allowing optical radiation to interact with the measured sheet, measuring at least one lignin dependent value on the basis of attenuation of the optical radiation of ultraviolet light or infrared region transmitted through the measured sheet in one or more predetermined optical absorption bands of lignin, measuring at least one dry matter dependent value on the basis of attenuation of the optical radiation interacted with the measured sheet at one or more predetermined optical absorption bands of dry matter, determining a general dependence of attenuation with respect to wavelength as a known type of function the parameters of which are based on the attenuation values at the measured wavelengths apart from the predetermined absorption bands of lignin and dry matter, two or more predetermined optical absorption bands fulfilling at least two of the following: a band each wavelength of which being longer than any of the wavelengths of the predetermined optical absorption bands of lignin and the dry matter, a band each wavelength of which being between one of the predetermined optical absorption bands of lignin and the dry matter, and a band each wavelength of which being shorter than any of the wavelengths of predetermined optical absorption bands of lignin and the dry matter, and forming a value representing a dry matter content on the basis of the at least one lignin dependent value, the at least one dry matter dependent value and the general dependence of attenuation.

21. The apparatus of claim 5, wherein the detector further includes a reflector.

* * * * *